(12) United States Patent
Kamata et al.

(10) Patent No.: US 10,309,940 B2
(45) Date of Patent: Jun. 4, 2019

(54) DATA PROCESSING DEVICE FOR CHROMATOGRAPH AND DATA PROCESSING METHOD FOR CHROMATOGRAPH

(71) Applicant: SHIMADZU CORPORATION, Kyoto-shi, Kyoto (JP)

(72) Inventors: Etsuho Kamata, Kyoto (JP); Toshinobu Yanagisawa, Kyoto (JP); Yasuhiro Mito, Kyoto (JP); Kenichi Mishima, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 464 days.

(21) Appl. No.: 14/902,638

(22) PCT Filed: Aug. 5, 2013

(86) PCT No.: PCT/JP2013/071156
§ 371 (c)(1),
(2) Date: Jan. 4, 2016

(87) PCT Pub. No.: WO2015/019400
PCT Pub. Date: Feb. 12, 2015

(65) Prior Publication Data
US 2016/0169848 A1    Jun. 16, 2016

(51) Int. Cl.
*G01N 30/86*    (2006.01)
(52) U.S. Cl.
CPC ................ *G01N 30/8634* (2013.01)
(58) Field of Classification Search
CPC ................................. G01N 30/8634
See application file for complete search history.

(56) References Cited

U.S. PATENT DOCUMENTS

| | | | | |
|---|---|---|---|---|
| 4,674,323 A | * | 6/1987 | Rulf | G01N 30/88 422/70 |
| 4,752,888 A | * | 6/1988 | Yoshihara | G06K 9/0053 702/32 |

(Continued)

OTHER PUBLICATIONS

The Japanese Pharmacopoeia Sixteenth Edition, (online), Mar. 24, 2011, Ministry of Health, Labour and Welfare, (searched on Sep. 25, 2012), Internet <URL: http://jpdb.nihs.go.jp/jp16/>, pp. 311-312.

(Continued)

*Primary Examiner* — Brigitte A Patterson
(74) *Attorney, Agent, or Firm* — Sughrue Mion, PLLC

(57) ABSTRACT

There are provided a data processing device for chromatograph and a data processing method for chromatograph which allow a peak to be desirably checked. A peak (correction target peak (P1)) whose intensity exceeds a predetermined threshold in a chromatogram at a target wavelength ($\lambda 1$) is corrected based on correction reference values (height (H1) and area (A1) of a peak (P11)) and a sensitivity coefficient (R=I1/I2), and the chromatogram after correction is displayed or printed. Therefore, even if the correction target peak (P1) is saturated, display or printing may be performed in a state where correction has been performed so that the chromatogram at the peak (P1) is not cut off in the middle. Accordingly, at the time of display or printing of the chromatogram, a fine peak may be prevented from becoming too small, and also the correction target peak (P1) may be prevented from being cut off in the middle, and thus the peaks may be desirably checked.

6 Claims, 6 Drawing Sheets

(56) References Cited

U.S. PATENT DOCUMENTS

| | | | |
|---|---|---|---|
| 5,214,593 A | 5/1993 | Magnussen, Jr. et al. | |
| 2007/0185659 A1* | 8/2007 | Love | G01N 30/88 |
| | | | 702/35 |
| 2012/0166101 A1* | 6/2012 | Lytle | G01N 30/861 |
| | | | 702/32 |

OTHER PUBLICATIONS

Written Opinion for PCT/JP2013/071156 dated Nov. 12, 2013. [PCT/ISA/237].

Communication dated Jun. 2, 2016, from the State Intellectual Property Office of People's Republic of China in counterpart Application No. 201380077284.8.

Michael D. Bond et al; "Evaluation of a Dual-Wavelength Size Exclusion HPLC Method With Improved Sensitivity to Detect Protein Aggregates and Its Use to Better Characterize Degradation Pathways of an IgG1 Monoclonal Antibody" Journal of Pharmaceutical Science, vol. 99, No. 6; pp. 2582-2597.

* cited by examiner

DATA PROCESSING DEVICE FOR CHROMATOGRAPH AND DATA PROCESSING METHOD FOR CHROMATOGRAPH

TECHNICAL FIELD

The present invention relates to a data processing device for chromatograph and a data processing method for chromatograph which are for processing three-dimensional data representing a relationship between time, wavelength and intensity obtained by analyzing a sample by a chromatograph.

BACKGROUND ART

With a liquid chromatograph, a gas chromatograph and the like, by irradiating measurement light on a sample inside a cell, for example, and by detecting transmitted light from the sample by a detector, chromatogram data representing the relationship between time and intensity (absorbance or the like) may be obtained. If a PDA detector (Photodiode Array Detector) is used as the detector, light from the sample dispersed by a diffraction grating or the like may be detected by a plurality of photodiodes for respective wavelengths, and thus three-dimensional data representing the relationship between time, wavelength and intensity may be obtained.

When an impurity analysis is performed for a pharmaceutical product by using this type of chromatograph, the proportion of impurities to a main component in a sample is sometimes analyzed. In this case, when the concentration difference of components in the sample is great, there are problems that, if a low-concentration component (impurity) is to be accurately detected, the signal of a high-concentration component (main component) is saturated, and if the high-concentration component (main component) is to be accurately detected, the low-concentration component (impurity) is buried in the noise.

For example, it is described in "Acetylcysteine, Purity (6) Related Substances" (pp. 311-312) in Non-Patent Document 1 that, if a test is conducted by a liquid chromatograph that uses an ultraviolet absorption photometer at a measurement wavelength of 220 nm, the areas of peaks other than acetylcysteine are each not more than 0.3%, and the total area is not more than 0.6%.

PRIOR ART DOCUMENTS

Non-Patent Documents

Non-Patent Document 1: The Japanese Pharmacopoeia Sixteenth Edition, (online), Mar. 24, 2011, Ministry of Health, Labour and Welfare, (searched on Sep. 25, 2012), Internet <URL: http://jpdb.nihs.go.jp/jp16/>

SUMMARY OF THE INVENTION

Problems to be Solved by the Invention

FIGS. 8(a) and 8(b) are diagrams for describing modes of display or printing of a conventional chromatogram. Conventionally, at the time of displaying or printing chromatogram data that is obtained at the time of analysis of a sample, the obtained data is displayed or printed as it is.

Accordingly, as shown in FIG. 8(a), in the case where a peak P101 of a main component is saturated, there is a problem that the chromatogram at the peak P101 is cut off in the middle, and the peak P101 cannot be desirably checked. Also, as shown in FIG. 8(b), in the case where the peak P101 of the main component is prevented from being saturated, a fine peak P102 of an impurity or the like becomes too small to be checked.

The present invention has been made in view of the above circumstances, and has its object to provide a data processing device for chromatograph and a data processing method for chromatograph which allow a peak to be desirably checked.

Means for Solving the Problems

A data processing device for chromatograph of the present invention is the data processing device being for processing three-dimensional data representing a relationship between time, wavelength and intensity obtained by an analysis of a sample by the chromatograph, the data processing device comprising: a correction target peak detection unit for detecting, as a correction target peak, a peak whose intensity exceeds a predetermined threshold in a chromatogram at a target wavelength; a correction reference value calculation unit for calculating, as a correction reference value, at least one of a height and an area of a peak, corresponding to the correction target peak, in a chromatogram at a correction reference wavelength different from the target wavelength; a sensitivity coefficient calculation unit for calculating, as a sensitivity coefficient, a ratio between intensity at the target wavelength and intensity at the correction reference wavelength based on a spectrum at a time different from a retention time of the correction target peak; a peak correction processing unit for correcting the correction target peak based on the correction reference value and the sensitivity coefficient; and an output processing unit for causing a chromatogram at the target wavelength for which the correction target peak has been corrected by the peak correction processing unit to be displayed or printed.

According to such a configuration, a peak (correction target peak) whose intensity exceeds a predetermined threshold in a chromatogram at the target wavelength may be corrected based on the correction reference value and the sensitivity coefficient, and the chromatogram after correction may be displayed or printed. Therefore, even if the correction target peak is saturated, display or printing may be performed in a state where correction has been performed so that the chromatogram at the peak is not cut off in the middle.

Accordingly, at the time of display or printing of the chromatogram, the fine peak may be prevented from becoming too small, and also the correction target peak may be prevented from being cut off in the middle, and thus the peaks may be desirably checked. As a result, the corrected peak (correction target peak) and the peak which is not corrected (fine peak) may be compared by looking at the chromatogram, and analysis of a sample may be desirably performed.

The output processing unit is preferable to output the correction target peak corrected by the peak correction processing unit in a different display mode or a different print mode from another part of the chromatogram.

According to such a configuration, the corrected peak (correction target peak) may be clearly distinguished from other parts of the chromatogram. Since the reliability of the corrected peak is low compared to a peak which is not corrected, analysis may be desirably performed if the corrected peak is clearly distinguished from other parts of the chromatogram and be recognized as a peak which has been corrected in advance.

The output processing unit may output the color or the type of line of the correction target peak corrected by the peak correction processing unit in a different display mode or print mode from other parts of the chromatogram.

A data processing method for chromatograph of the present invention is the data processing method being for processing three-dimensional data representing a relationship between time, wavelength and intensity obtained by an analysis of a sample by the chromatograph, the data processing method comprising: a correction target peak detection step of detecting, as a correction target peak, a peak whose intensity exceeds a predetermined threshold in a chromatogram at a target wavelength; a correction reference value calculation step of calculating, as a correction reference value, at least one of a height and an area of a peak, corresponding to the correction target peak, in a chromatogram at a correction reference wavelength different from the target wavelength; a sensitivity coefficient calculation step of calculating, as a sensitivity coefficient, a ratio between intensity at the target wavelength and intensity at the correction reference wavelength based on a spectrum at a time different from a retention time of the correction target peak; a peak correction processing step of correcting the correction target peak based on the correction reference value and the sensitivity coefficient; and an output processing step of causing a chromatogram at the target wavelength for which the correction target peak has been corrected in the peak correction processing step to be displayed or printed.

In the output processing step, the correction target peak corrected in the peak correction processing step is preferable to be output in a different display mode or a different print mode from another part of the chromatogram.

Effects of the Invention

According to the present invention, at the time of displaying or printing a chromatogram, a fine peak may be prevented from becoming too small, and also a correction target peak may be prevented from being cut off in the middle, and thus peaks may be desirably checked.

MODE FOR CARRYING OUT THE INVENTION

Figure 1:
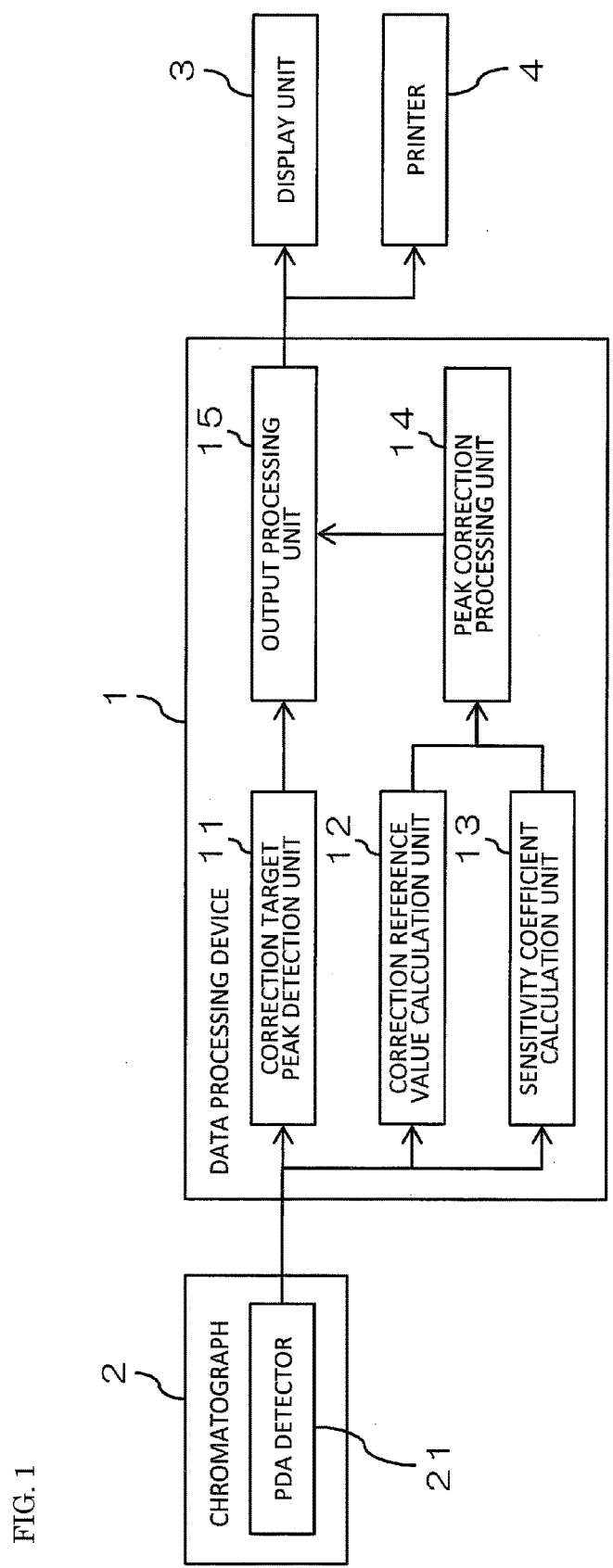
FIG. 1 is a block diagram showing an example configuration of a data processing device according to an embodiment of the present invention.

FIG. 1 is a block diagram showing an example configuration of a data processing device 1 according to an embodiment of the present invention. The data processing device 1 is a data processing device for chromatograph, and is for processing data that is obtained by analyzing a sample by a chromatograph 2, and is capable of causing processed data to be displayed by a display unit 3 or to be printed by a printer 4. The chromatograph 2 may be a liquid chromatograph or a gas chromatograph.

A PDA detector 21 is provided to the chromatograph 2, for example. At the time of analysis of a sample, measurement light is irradiated on the sample inside a cell, for example, and transmitted light from the sample is detected by the PDA detector 21. The PDA detector 21 is provided with a plurality of photodiodes as photodetectors, and is capable of inputting, to the data processing device 1, three-dimensional data representing the relationship between time, wavelength and intensity (for example, absorbance), by detecting light from the sample which has been dispersed by a diffraction grating or the like by the plurality of photodiodes for respective wavelengths. Incidentally, the detector provided to the chromatograph 2 is not limited to the PDA detector 21, and may be another detector.

The data processing device 1 is configured by a computer including a CPU (Central Processing Unit), for example. The data processing device 1 according to the present embodiment functions as a correction target peak detection unit 11, a correction reference value calculation unit 12, a sensitivity coefficient calculation unit 13, a peak correction processing unit 14, an output processing unit 15 and the like by the CPU executing programs.

Figure 2:
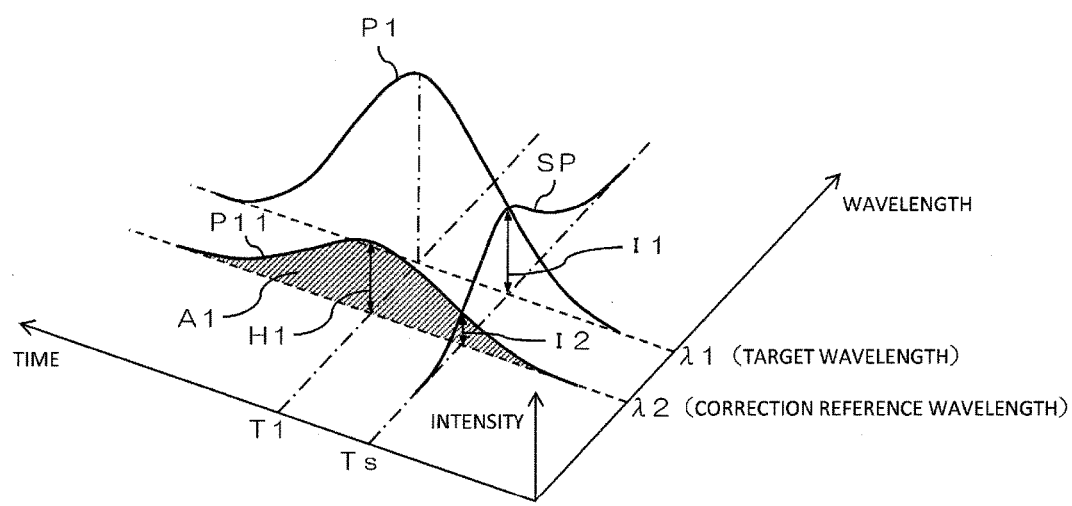
FIG. 2 is a diagram for describing three-dimensional data that is obtained by analyzing a sample by a chromatograph.

FIG. 2 is a diagram for describing three-dimensional data that is obtained by analyzing a sample by the chromatograph 2. In this example, a peak P1 with relatively high intensity appears at a time T1 in a chromatogram at a wavelength $\lambda 1$. In such a case, the peak P1 may be saturated, and the chromatogram that is displayed on the display unit 3 or the chromatogram that is printed by the printer 4 is possibly cut off in the middle.

Accordingly, in the present embodiment, the wavelength $\lambda 1$ is taken as a target wavelength, and the peak P1 as a correction target peak may be corrected based on a peak P11, corresponding to the peak 1, in a chromatogram at a wavelength (correction reference wavelength $\lambda 2$) different from the target wavelength $\lambda 1$ and a spectrum SP at a time Ts different from a retention time T1 of the peak P1, and a chromatogram with a corrected peak P1 may be displayed or printed.

Referring back to FIG. 1, the correction target peak detection unit 11 detects, based on the three-dimensional data input from the PDA detector 21 of the chromatograph 2, whether there is a peak that exceeds a predetermined threshold. Then, if there is a peak whose intensity exceeds a predetermined threshold in the chromatogram at the target wavelength $\lambda 1$, this peak is detected as the correction target peak P1. The threshold may be set to a value smaller than the intensity at which the peak is saturated.

The correction reference value calculation unit 12 calculates, for the peak P11, corresponding to the correction target peak P1, in the chromatogram at the wavelength (correction reference wavelength $\lambda 2$) different from the target wavelength $\lambda 1$, a height H1 and an area A1 of the peak P11 as the correction reference values (see FIG. 2). As the correction reference wavelength λ2, a wavelength for which linearity may be obtained with respect to the concentration and the intensity detected by the PDA detector 21 is selected, for example. Here, the peak P11 corresponding to the correction target peak P1 is a peak appearing at the same retention time (time T1) as the correction target peak P1, and is a peak of the same component as the correction target peak P1.

The sensitivity coefficient calculation unit 13 calculates a sensitivity coefficient R that is used to correct the correction target peak P1, based on the spectrum SP at the time Ts different from the retention time T1 of the correction target peak P1. As shown in FIG. 2, as the time Ts, a time at the tail of the correction target peak P1 is selected. The sensitivity coefficient R is calculated as the ratio between an intensity I1 at the target wavelength λ1 and an intensity I2 at the correction reference wavelength λ2 in the spectrum SP cut out at the tail of the correction target peak P1 (see FIG. 2).

The peak correction processing unit 14 calculates a peak height H2 and a peak area A2 for the correction target peak P1 based on the correction reference values (the height H1 and the area A1 of the peak P11) calculated by the correction reference value calculation unit 12 and the sensitivity coefficient R calculated by the sensitivity coefficient calculation unit 13. Then, the correction target peak P1 is corrected by the peak height and the peak area of the correction target peak P1 being replaced by the peak height H2 and the peak area A2.

The output processing unit 15 displays or prints the chromatogram at the target wavelength λ1 by outputting the data to the display unit 3 or the printer 4. At this time, the output processing unit 15 may display on the display unit 3 or print by the printer 4 the chromatogram in which the correction target peak P1 detected by the correction target peak detection unit 11 has been corrected by peak correction processing unit 14. Also, the output processing unit 15 may change the display mode or the print mode of the chromatogram.

Figure 3:
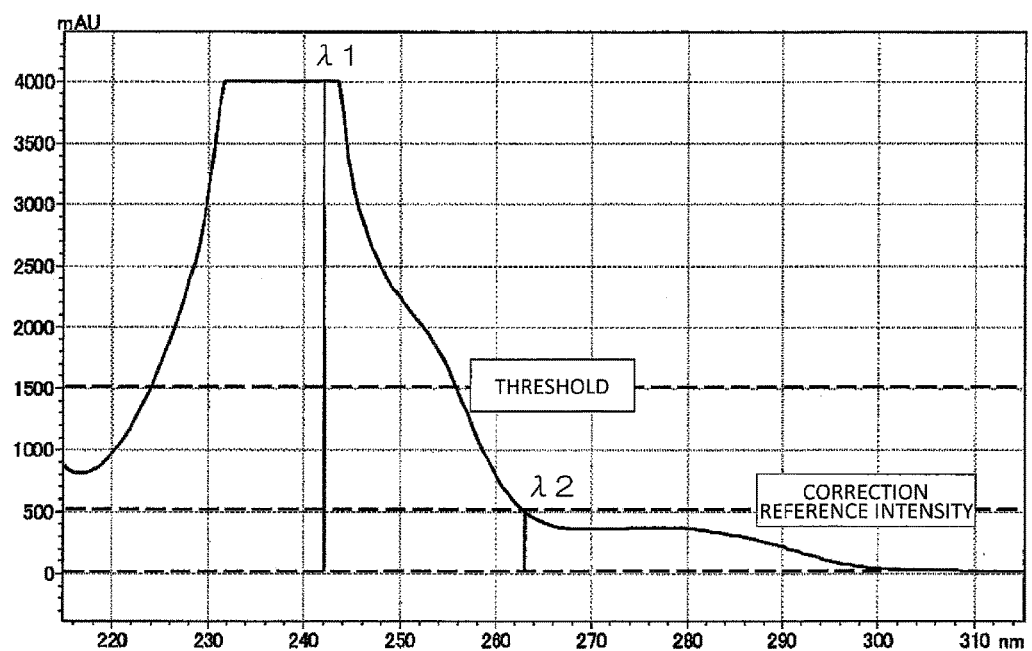
FIG. 3 is a diagram for specifically describing a mode of correction of a correction target peak, and shows a spectrum at a retention time of the correction target peak.
Figure 4:
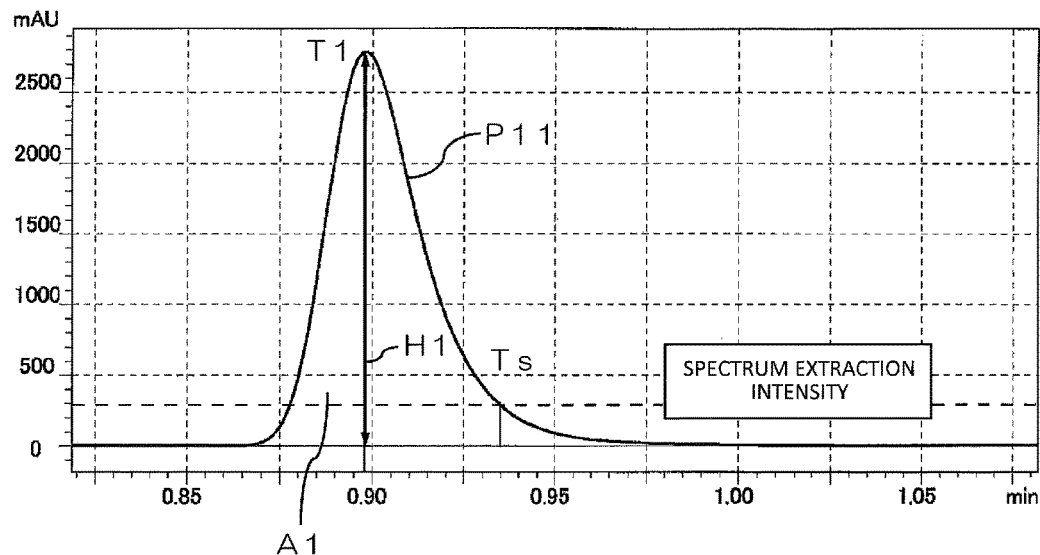
FIG. 4 is a diagram for specifically describing a mode of correction of a correction target peak, and shows a chromatogram at a correction reference wavelength.
Figure 5:
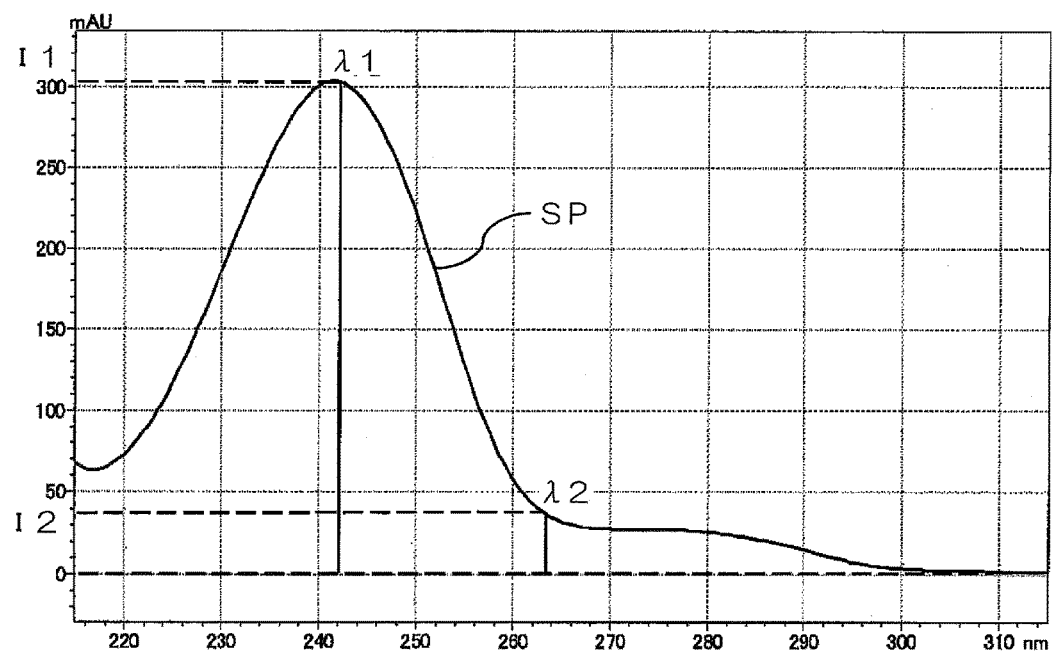
FIG. 5 is a diagram for specifically describing a mode of correction of a correction target peak, and shows a spectrum at a time different from the retention time of the correction target peak.

FIGS. 3 to 5 are diagrams for specifically describing a mode of correction of the correction target peak P1, and FIG. 3 shows a spectrum at the retention time T1 of the correction target peak P1, FIG. 4 shows a chromatogram at the correction reference wavelength λ2, and FIG. 5 shows a spectrum SP at the time Ts different from the retention time T1 of the correction target peak P1.

First, at the time of determining the correction reference wavelength λ2, a spectrum at the retention time T1 of the correction target peak P1 as shown in FIG. 3 is used. Specifically, a wavelength λ2 of a predetermined correction reference intensity is determined in the spectrum as the correction reference wavelength. Additionally, the correction reference intensity is a value that is set in advance as intensity that is lower than a threshold that is used at the time of detecting the correction target peak P1.

Then, correction reference values are calculated by using a chromatogram at the correction reference wavelength λ2 as shown in FIG. 4. That is, the height H1 and the area A1 of the peak P11 in the chromatogram corresponding to the correction target peak P1 are calculated as the correction reference values. The time Ts (time different from the retention time T1 of the correction target peak P1) that is used as the reference at the time of extracting the spectrum SP to be used for calculation of the sensitivity coefficient R may be determined as a time when predetermined spectrum extraction intensity is reached in the chromatogram.

A spectrum SP at the time Ts as shown in FIG. 5 is extracted based on the time Ts determined in the above manner, and the sensitivity coefficient R is calculated by using the spectrum SP. Specifically, the sensitivity coefficient R may be calculated by the following formula (1) based on the intensity I1 at the target wavelength λ1 and the intensity I2 at the correction reference wavelength λ2 in the spectrum SP.

Sensitivity coefficient $R$=intensity $I1$/intensity $I2$     (1)

Basically, a spectrum has a shape that is unique to a component, and the shape is not changed based on the degree of concentration. In a chromatogram, due to this similarity of the spectrum shapes, the heights and the areas of chromatogram peaks at respective wavelengths belonging to one spectrum peak have a fixed relation to one another.

Accordingly, as shown by the following formulae (2) and (3), by multiplying the correction reference values (the height H1 and the area A1 of the peak P11) calculated by using the chromatogram at the correction reference wavelength λ2 by the sensitivity coefficient R determined in the above manner, a peak height H2 and a peak area A2 of the correction target peak P1 may be calculated as correction values.

Peak height $H2$=peak height $H1$×sensitivity coefficient $R$     (2)

Peak area $A2$=peak area $A1$×sensitivity coefficient $R$     (3)

Figure 6:
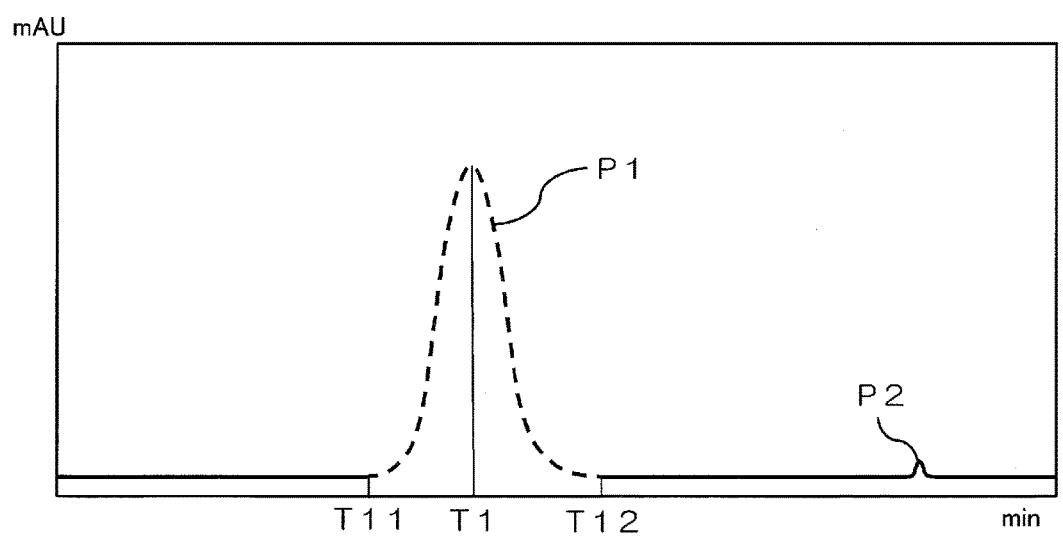
FIG. 6 is a diagram showing an example of a display mode or a print mode of a chromatogram with a corrected correction target peak.

FIG. 6 is a diagram showing an example of a display mode or a print mode of a chromatogram with a corrected correction target peak P1. A peak of a main component (correction target peak P1), which is the analysis target, and a peak of an impurity component or the like (fine peak P2) appear in this chromatogram.

Figure 8A:
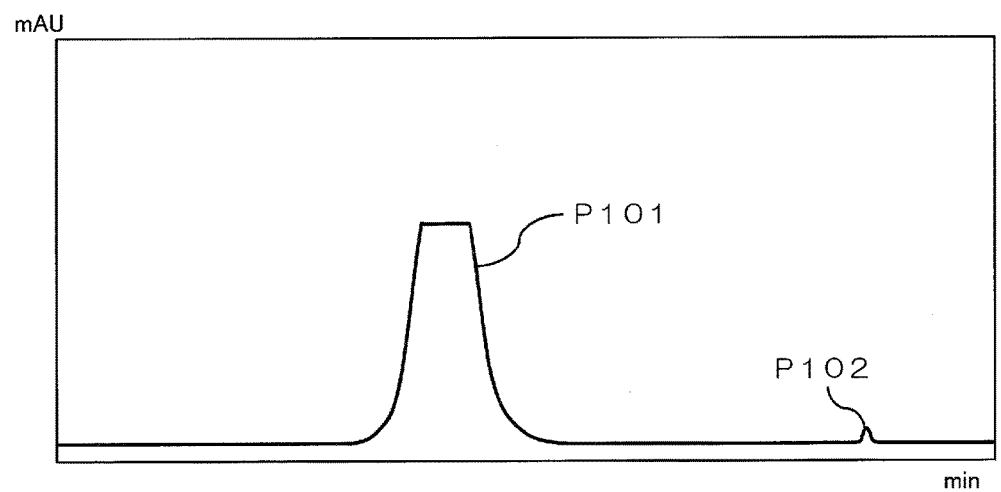
FIGS. 8(a) and 8(b) are diagrams for describing modes of display or printing of a conventional chromatogram.
Figure 8B:
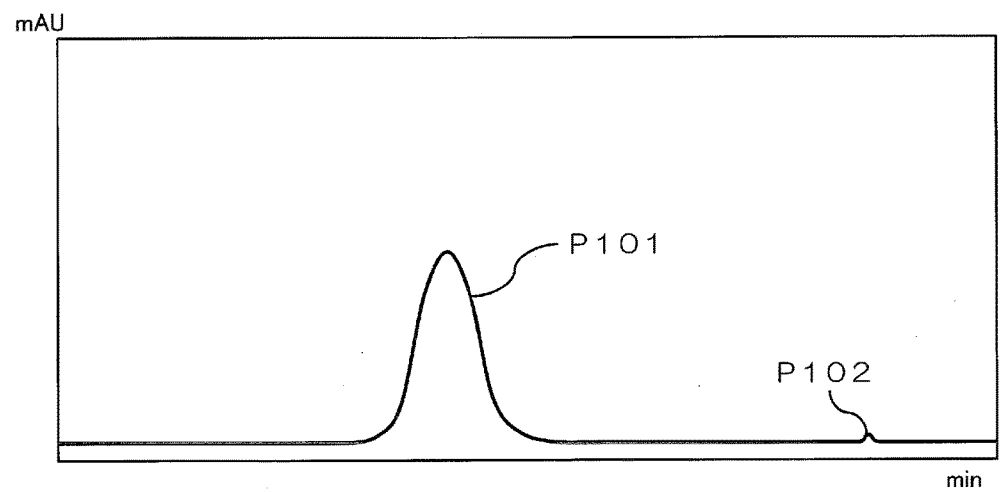

In the chromatogram shown in FIG. 6, the correction target peak P1 (from a start time T11 to an end time T12 of the peak) is corrected, and thus the peak P101 of the main component would not be saturated and be cut off in the middle as in FIG. 8(a), or the fine peak P102 would not be so small as to be difficult to be checked as in FIG. 8(b).

In this manner, according to the present embodiment, a peak (correction target peak P1) whose intensity exceeds a predetermined threshold in a chromatogram at the target wavelength λ1 may be corrected based on the correction reference values (the height H1 and the area A1 of the peak P11) and the sensitivity coefficient R, and the chromatogram after correction may be displayed or printed. Therefore, even if the correction target peak P1 is saturated, display or printing may be performed in a state where correction has been performed so that the chromatogram at the peak P1 is not cut off in the middle Accordingly, at the time of display or printing of the chromatogram, the fine peak P2 may be prevented from becoming too small, and also the correction target peak P1 may be prevented from being cut off in the middle, and thus the peaks P1 and P2 may be desirably checked. As a result, the corrected peak (correction target peak P1) and the peak which is not corrected (fine peak P2) may be compared by looking at the chromatogram, and analysis of a sample may be desirably performed.

As shown in FIG. 6, according to the present embodiment, the correction target peak P1 which has been corrected is displayed or printed with a broken line unlike other parts of the chromatogram shown by solid lines. However, the correction target peak P1 which has been corrected may be displayed or printed with other types of lines (including thickness and the like) instead of a broken line, or may be displayed or printed with different colors as long as the correction target peak P1 which has been corrected is output in a different display mode or print mode from other parts of the chromatogram.

The corrected peak (correction target peak P1) may thus be clearly distinguished from other parts of the chromatogram. Since the reliability of the corrected peak is low compared to a peak which is not corrected, analysis may be desirably performed if the corrected peak is clearly distinguished from other parts of the chromatogram and be recognized as a peak which has been corrected.

Figure 7:
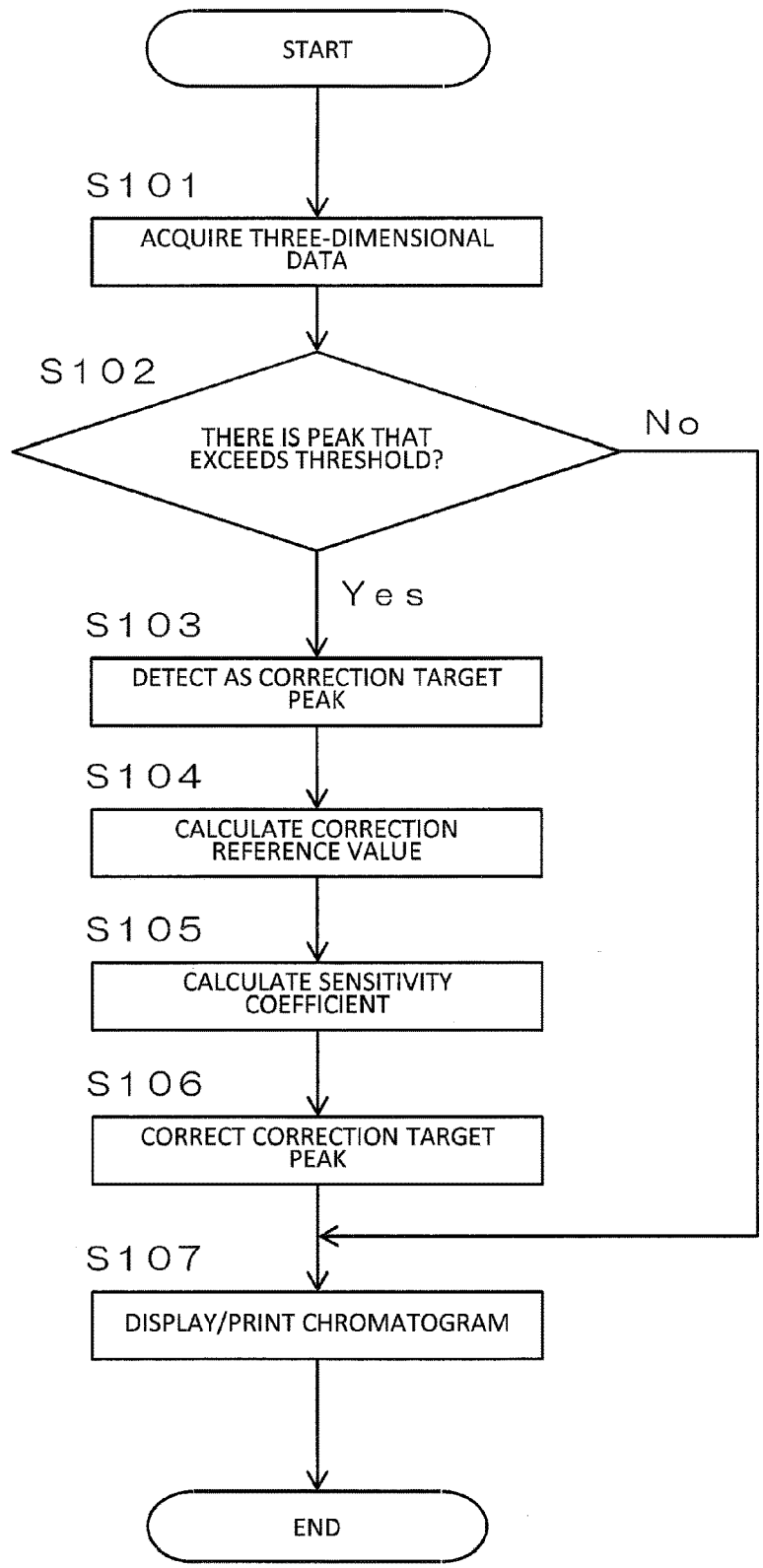
FIG. 7 is a flow chart showing an example of a process that is performed by the data processing device at the time of display or printing of a chromatogram with a corrected correction target peak.

FIG. 7 is a flow chart showing an example of a process that is performed by the data processing device 1 at the time of display or printing of a chromatogram with a corrected correction target peak P1. The data processing device 1 acquires three-dimensional data from the PDA detector 21 of the chromatograph 2 (step S101), and then determines whether there is a peak that exceeds a predetermined threshold in the target wavelength $\lambda 1$ of the three-dimensional data (step S102).

In the case where a peak that exceeds the predetermined threshold is not detected (No in step S102), the acquired three-dimensional data is used as it is, and the chromatogram at the target wavelength $\lambda 1$ is displayed or printed (step S107). In the case where a high-intensity peak that exceeds the threshold is not present, the chromatogram is not cut off in the middle due to saturation of the peak even if the chromatogram is displayed or printed as it is.

On the other hand, in the case where a peak that exceeds the predetermined threshold is detected (Yes in step S102), this peak is detected as the correction target peak P1 (step S103: correction target peak detection step). Then, the height H1 and the area A1 of the peak P11, corresponding to the correction target peak P1, in the chromatogram at the correction reference wavelength $\lambda 2$ different from the target wavelength $\lambda 1$ are calculated as the correction reference values (step S104: correction reference value calculation step).

Then, the ratio between the intensity I1 at the target wavelength $\lambda 1$ and the intensity I2 at the correction reference wavelength $\lambda 2$ are calculated as the sensitivity coefficient R based on the spectrum SP at the time Ts different from the retention time T1 of the correction target peak P1 (step S105: sensitivity coefficient calculation step). The correction target peak P1 is corrected based on the correction reference values (the height H1 and the area A1 of the peak P11) and the sensitivity coefficient R calculated in the above manner (step S106: peak correction processing step), and a chromatogram with the corrected correction target peak P1 is displayed or printed (step 107: output processing step).

The above-described embodiment describes a case where both the height H1 and the area A1 of the peak P11, corresponding to the correction target peak P1, in the chromatogram at the correction reference wavelength $\lambda 2$ different from the target wavelength $\lambda 1$ are calculated as the correction reference values. However, such a configuration is not restrictive, and a configuration is also possible where only one of the height H1 and the area A1 of the peak P11 is calculated as the correction reference value, and where the correction target peak P1 is corrected based on this correction reference value and the sensitivity coefficient R.

Also, the above-described embodiment describes a configuration where a chromatogram may be displayed by the display unit 3 or be printed by the printer 4, but the output processing unit 15 may alternatively be configured to be capable of outputting data to only one of the display unit 3 and the printer 4.

DESCRIPTION OF REFERENCE SIGNS 1 data processing device
2 chromatograph
3 display unit
4 printer
11 correction target peak detection unit
12 correction reference value calculation unit
13 sensitivity coefficient calculation unit
14 peak correction processing unit
15 output processing unit
21 PDA detector
P1 peak (correction target peak)
P11 peak
SP spectrum
H1 height
A1 area
I1 intensity
I2 intensity

The invention claimed is:

1. A chromatograph system comprising:
 a chromatograph configured to analyze a sample inside the chromatograph and output three-dimensional data representing a relationship between time, wavelength and intensity; and
 a data processing device configured to process the three-dimensional data outputted by the chromatograph, the data processing device comprising:
 a correction target peak detection unit implemented by a CPU of the data processing device which detects, as a correction target peak, a peak whose intensity exceeds a predetermined threshold in a chromatogram at a target wavelength;
 a correction reference value calculation unit implemented by the CPU which calculates, as a correction reference value, at least one of a height and an area of a peak, corresponding to the correction target peak, in a chromatogram at a correction reference wavelength different from the target wavelength;
 a sensitivity coefficient calculation unit implemented by the CPU which calculates, as a sensitivity coefficient, a ratio between intensity at the target wavelength and intensity at the correction reference wavelength based on a spectrum at a time different from a retention time of the correction target peak;
 a peak correction processing unit implemented by the CPU which corrects the correction target peak based on the correction reference value and the sensitivity coefficient; and
 an output processing unit implemented by the CPU which causes a chromatogram at the target wavelength for which the correction target peak has been corrected by the peak correction processing unit to be displayed or printed.

2. The chromatograph system according to claim 1, wherein the output processing unit outputs the correction target peak corrected by the peak correction processing unit in a different display mode or a different print mode from another part of the chromatogram that includes another peak.

3. A chromatograph analysis method for a chromatograph system, including a chromatograph and a data processing device, to process three-dimensional data representing a relationship between time, wavelength and intensity obtained by an analysis of a sample by the chromatograph, the method comprising:

an analyzing step of analyzing the sample with the chromatograph; an outputting step of outputting the three-dimensional data with the chromatograph; and a processing step of processing the three-dimensional data with the data processing device, the processing step comprising:

a correction target peak detection step executed by a CPU of the data processing device, the correction target peak detection step comprising detecting, as a correction target peak, a peak whose intensity exceeds a predetermined threshold in a chromatogram at a target wavelength;

a correction reference value calculation step executed by the CPU, the correction reference value calculation step comprising calculating, as a correction reference value, at least one of a height and an area of a peak, corresponding to the correction target peak, in a chromatogram at a correction reference wavelength different from the target wavelength;

a sensitivity coefficient calculation step executed by the CPU, the sensitivity coefficient calculation step comprising calculating, as a sensitivity coefficient, a ratio between intensity at the target wavelength and intensity at the correction reference wavelength based on a spectrum at a time different from a retention time of the correction target peak;

a peak correction processing step executed by the CPU, the peak correction processing step comprising correcting the correction target peak based on the correction reference value and the sensitivity coefficient; and an output processing step executed by the CPU, the output processing step comprising causing a chromatogram at the target wavelength for which the correction target peak has been corrected in the peak correction processing step to be displayed or printed.

4. The chromatograph analysis method according to claim 3, wherein, in the output processing step, the correction target peak corrected in the peak correction processing step is output in a different display mode or a different print mode from another part of the chromatogram that includes another peak.

5. The chromatograph system according to claim 1, wherein the output processing unit causes the chromatogram to be displayed or printed such that an entire peak of the correction target peak, that is corrected by the peak correction processing unit, and another peak of the chromatograph may be compared by looking at the chromatogram that is displayed or printed.

6. The chromatograph analysis method according to claim 3, wherein, in the output processing step, the chromatogram is displayed or printed such that an entire peak of the correction target peak, that is corrected in the peak correction processing step, and another peak of the chromatograph may be compared by looking at the chromatogram that is displayed or printed.

* * * * *